United States Patent
de Acosta Del Rio et al.

(10) Patent No.: US 6,891,023 B1
(45) Date of Patent: May 10, 2005

(54) ANTIBODIES AND FV FRAGMENT RECOGNIZING ANTIGEN IOR C2

(75) Inventors: Cristina Maria Mateo de Acosta Del Rio, Ciudad Habana (CU); Lourdes Tatiana Roque Navarro, Ciudad Habana (CU); Alejo Morales Morales, Ciudad Habana (CU); Rolando Pérez Rodríguez, Ciudad de la Habana (CU); Marta Ayala Ávila, Ciudad de la Habana (CU); Jorge Victor Gavilondo Cowley, Ciudad de la Habana (CU); Marta Dueñas Porto, Ciudad de la Habana (CU); Hanssel Bell García, Ciudad de la Habana (CU); Enrique Rengifo Calzado, Ciudad de la Habana (CU); Normando Iznaga Escobar, Ciudad de la Habana (CU); Mayra Ramos Zuzarte, Ciudad de la Habana (CU)

(73) Assignee: Centro Inmunologia Molecular (CU)

( * ) Notice: Subject to any disclaimer, the term of this patent is extended or adjusted under 35 U.S.C. 154(b) by 0 days.

(21) Appl. No.: 09/889,480
(22) PCT Filed: Nov. 16, 2000
(86) PCT No.: PCT/CU00/00004
§ 371 (c)(1),
(2), (4) Date: Sep. 20, 2001
(87) PCT Pub. No.: WO01/36485
PCT Pub. Date: May 25, 2001

(30) Foreign Application Priority Data

Nov. 16, 1999 (CU) .............................................. 196/99

(51) Int. Cl.$^7$ ............................................. C07K 16/00
(52) U.S. Cl. ............................ 530/387.3; 530/388.85; 530/391.3; 424/133.1; 424/156.1
(58) Field of Search ................................ 530/300, 350, 530/387.1, 387.3, 388.1, 388.8, 388.85, 391.1, 391.3; 424/130.1, 133.1, 135.1, 155.1, 156.1, 178.1, 180.1, 181.1, 183.1; 435/326, 328

(56) References Cited

U.S. PATENT DOCUMENTS 5,712,120 A    1/1998  Rodriguez et al.

FOREIGN PATENT DOCUMENTS

| WO | WO 91/09967 | * 7/1991 |
| WO | WO97/33196 | 9/1997 |

OTHER PUBLICATIONS

Paul fundamental Immunolgy, Raven Press, chapter 8, p. 242, 1993.*
Panka et al PNAS 85:3080–84, 1988.*
Amit et al Science 233:747, 1986.*
Rudikoff et al PNAS 79:1979–1983, 1982.*
Bird et al Science 242:423, 1988.*
Riechmann et al Nature 332:323,1988.*
Immunologia 14: 130–132, 1995, Characterization of IOR C5 Colorectal Tumor Associated Antigen, Vazques et al.
Nature vol. 332, pp. 323–327, Reshaping Human Antibodies for Therapy, 1988, Jongs et al.

* cited by examiner

Primary Examiner—Larry R. Helms
(74) Attorney, Agent, or Firm—Lackenbach Siegel, LLP (57) ABSTRACT

Novel recombinant antibodies from murine antibody IOR C5 produced by the hybridoma deposited with the ECCC 97061101. The recombinant antibodies were obtained using recombinant DNA technology and are characterized in that they recognize antigen ior C2. The recombinant antibodies are specifically chimeric antibody, humanized antibody, and single chain Fv fragment. The chimeric antibody contains the variable domains of the murine immunoglobuline and the constant regions of the human immunoglobuline. The humanized antibody contains the constant regions of human immunoglobuline and has been specifically modified in the murine frameworks regions (FRs) and within the latter, in those areas that may result in an antigenic site for cells T. The Fv fragment contains the variable domains of murine immunoglobuline. The invention also relates to the utilization of recombinant antibodies derived from murine antibody ior C5 in the diagnosis and therapy of colorectal tumors, the metastasis thereof and recurrences.

12 Claims, 1 Drawing Sheet

FIGURE 1

ANTIBODIES AND FV FRAGMENT RECOGNIZING ANTIGEN IOR C2

FIELD OF THE INVENTION

This invention is related to the field of the biotechnology and in particular with new recombinant antibodies obtained using genetic engineering technology, specifically with a chimeric antibody, a humanized antibody and a single chain Fv fragment obtained from murine ior C5 antibody, which recognize epitopes expressed in ior C2 antigen which has been characterised as glycoprotein complex which is expressed in normal and malignant colorectal cells.

BACKGROUND OF THE INVENTION

They have been tested different forms of colorectal carcinoma treatment, however up to day the surgery it has been the only curative way. The surgery has allowed reaching higher percents of survival, when the detection of the tumour is in an early stage, but unfortunately the most cases are diagnosticated when the tumour has metastized.

In this moment, the strategy to increase survival includes the diagnosis, the therapeutic and epidemiology, in stages wherein it has not been produced the dissemination of the disease to external layers of the organs and the tumour is still surgically curable. In the way, the knowledge of epidemiological factors as well as the development of new therapeutically methods will help to increase the survival.

The use of monoclonal antibodies (Mabs) or their fragments, labelled with radioactive isotopes for the detection of cancer through immunogammagraphic methods, has been used in the last years. The Mabs have shown potential to be used as carriers of radioisotopes and to be targeted to the associated tumour antigens.

Some of the radiolabelled antibodies have been used to detect tumours associated with carcinoembrionary antigens (CEA). The antibodies against CEA, labelled with I-131 or I-125 are used to detect tumours producing CEA or associated with this marker (U.S. Pat. No. 3,663,684, U.S. Pat. No. 3,867,363 y U.S. Pat. No. 3,927,193). Also, Mabs can be labelled with Tc-99m to get molecules for "in vivo" diagnosis.

The development of the hybridoma antibody technique by Köhler and Milstein revolutionised the discipline of immunochemistry and provided a new family of reagents with potential applications in the research and clinical diagnosis of diseases (Köhler G; Milstein C. (1975) Nature 256, 495–497). These antibodies have not shown strong therapeutic efficacy, while it has become routine to produce mouse monoclonal antibodies (mAbs) for use in basic research and clinical diagnosis, it has been difficult to use these for "in vivo" immunotherapy, because they have reduced half life in humans, poor recognition of mouse antibodies effector domains by the human immune system and also because foreign immunoglobulins can elicit an antiglobulin response (HAMA response) that may interfere with therapy.

The development of the genetic engineering has revolutionised the ability to genetically manipulate antibody genes and then to produce mAbs having decreased or eliminated antigenicity and enhanced desired effector functions, when these antibodies are used in the treatment or diagnosis of some pathologies. These manipulations have provided an alternative where a murine mAb can be converted to a predominantly human form with the same antigen binding properties (Morrison S. L; et al 1984, P.N.A.S. USA, 81,6851–6855).

Recently they have been developed some methods in order to humanise murine or rat antibodies and decrease xenogenic response against foreign proteins when they are used in humans.

One of the first intents to reduce antigenicity, has been by producing "chimeric" antibodies. In these molecules, the variable domains were inserted into human frameworks, in this way not only it can be reached the decrease of the immunogenicity but also the improvement of effector functions, because they are humans and therefore recognised by the immune system (Morrison S. L et al (1984) P.N.A.S, USA 81, 6851–6855). These chimeric molecules retain the recognition of the original antigen and its constant region is not immunogenic, although the immunogenicity against murine variable region is retained.

Other authors have attempted to build rodent antigens binding sites directly into human antibodies by transplanting only the antigen binding site, rather than the entire variable domain, from a murine antibody (Jones P. T et al (1986) Nature 321, 522–524, Verhoeyen M et al (1988) Science 239, 1534–1536). They have been developed some applications of this method by Rietchmann (Rietchmann L. et al (1988) Nature 332, 323–327; Quee C. et al (1989) P.N.A.S USA 86,10029–10033), however other authors have worked with reshaped antibodies, which included some murine residues in human FRs in order to recover the affinity for the original antigen (Tempest, P. R (1991) Biotechnology 9, 266–272).

Mateo et al. (U.S. Pat. No. 5,712,120) described a procedure to reduce immunogenicity of the murine antibodies. In this procedure, the modifications are restricted to the variable domains and specifically to the murine frameworks of the chimeric antibodies. Even more, these modifications are only carried out in the FRs regions with amphipatic helix structure, therefore are potential epitopes recognised by T cells. The method proposes to substitute the murine residues inside the amphipatic regions, by the amino acids in the same positions in the human immunoglobulines, of course the amino acids involved in the tridimentional structure of the binding site, it means Verniers zone, canonical structures of the CDRs and the amino acid of the inter-phase between light and heavy chain are excluded.

The antibody modified by the method described by Mateo et al, retains the capacity of the recognition and binding to the antigen, that recognised the original antibody and it results less immunogenic because of this it is got an increase of the therapeutic efficacy. Through this procedure only few mutations are necessary to obtain modified antibodies that shown reduced immunogenicity compared with chimeric antibodies.

The IOR C5 murine monoclonal antibody (patent application WO 97/33916) is an IgG1 isotype, obtained from immunisation of Balb/c with SW1116 cells (colorectal adenocarcinoma), recognised an antigen expressed preferentially in the surface and cytoplasm of the malignant and normal colorectal cells. This antibody does not recognise neither CEA, Lewis a, Lewis b, asialylated Lewis, membranes of normal mononuclear cells antigens nor red globules (Vazquez A. M. et al, Hybridoma 11, pag. 245–256, 1992).

Western blotting studies using SW1116 membranes extract showed that this antibody recognized a glycoprotein complex which was denominated ior C2, with two molecular weight forms (145 and 190 Kda) (Vázquez A. M. et al, Year Immunol. Basel, Karger, vol. 7, pag. 137–145,1993).

Also it is known from the state of the art that using genetic engineering techniques, recombinant fragments can be constructed from monoclonal antibodies. There are many reports validating the use of different antibody fragments in the "in vivo" diagnosis and the therapeutic of the diseases.

Ira Pastan et al. (EP 0796334 A1) describes the construction of single chain Fv fragments, using variables regions of antibodies that specifically recognised carbohydrates related with Lewis Y antigen. Using these fragments, he developed a method to detect cells bearing this antigen. Also, he gives evidences of the inhibitor effect of these fragments on cells bearing the antigen.

DISCLOSURE OF THE INVENTION

This invention is related to recombinant antibodies obtained using genetic engineering technology, specifically with a chimeric antibody, a humanised antibody and a single chain Fv fragment obtained from murine antibody IOR C5 antibody, produced by the hybridoma of the same name deposited in correspondence with the Budapest Treaty under accession number ECCC 97061101 with European Collection of Cell Cultures, on Jun. 11, 1997. This antibody recognizes epitopes expressed in ior C2 antigen, which is a glycoprotein complex that it is expressed in normal and malignant colorectal cells.

DETAILED DESCRIPTION OF THE INVENTION cDNA Synthesis and Gene Amplification of the Variable Region of Murine C5.

Cytoplasmic RNA was extracted from about 106 hybridoma cells of the monoclonal antibody C5 (Vázquez A. M. et al. Year Immunol, Basel, Karger, vol 7, pag. 137–145, 1993). The method used to extract RNA was described by Faloro et al (Faloro, J., Treisman, R., and Kemen, R. (1989). Methods in Enzymology 65:718–749).

The cDNA synthesis reaction consisted of 5 ug RNA, obtained with 25 pmoles of the designed primers to hybridise in the beginning of the constant region of murine IgG1, and in the murine constant kappa region for the light chain, 2.5 mM each of deoxinucleotide (dNTPs), 50 mM Tris-Hcl pH 7.5, 75 mM KCl, 10 mM DTT, 8 mM MgCl2 and 15 u of ribonuclease inhibitor (RNA guard, Pharmacia) in a total volume of 50 ul. Samples were heated at 700 C, for 10 min and slowly cooled to 370 C over a period of 30 min. Then, 100 units reverse transcriptase were added and the incubation at 420 C continued for 1 hour.

The variable regions of light chain (VK) and heavy chain VH) were amplified using Polymerase Chain Reaction (PCR). Briefly, 5 μl cDNA of VH or VK were mixed with 25 pmoles of specific primers, 2.5 mM each of dNTP, 5 μl buffer 10× for the enzyme DNA polymerase and 1 unit of this enzyme. Samples were subjected to 25 thermal cycles at 940 C, 30 sec; 500 C, 30 sec; 720 C, 1 min; and a last incubation for 5 min at 720 C.

Cloning and Sequencing of Amplified cDNA.

The purified VH and VK cDNA were cloned into TA vector (TA Cloning kit. Promega, USA). Clones were sequenced by the dideoxy method using T7 DNA Pol (Pharmacia, Sweden).

Construction of Chimeric Genes.

The light and heavy chains variable regions were obtained by enzyme restrictions from TA vectors and cloned into expression vectors (Coloma M. J. et al., Journal of Immunological Methods, 152, 89–104,1992).

The VH genes were cut from TA vector by EcoRV and NheI digestion, and cloned in PAH 4604 expression vector, an human constant IgG1 is included and histidinol resistance gene.

The resultant construction is C5VH-PAH4604. The VK genes were cut from TA EcoRV and SalI digestion and cloned In PAG4622. This vector contains resistance to the gpt and used kappa human constant region. The resultant construction is C5VK-PAG4622.

Chimeric Antibody Expression.

NSO cells were electroporated with 10 μg of C5VH-PAH4604 and 10 ug of C5VK-PAG4622 and linearized by digestion with Pvul. The DNAs were mixed together, ethanol precipitated and dissolved in 25 μl water. Approximately 107 NSO cells were grown to semiconfluency, harvested by centrifugation and resuspended in 0.5 ml DMEN together with the digested DNA in an electroporation cuvette. After 5 minutes on ice, the cells were given a pulse of 170 volts and 960° F.) and left in ice for a further 30 minutes. The cells were then put Into 20 ml DMEN plus 10% foetal calf serum and allowed recovering for 48 hours. At this time the cells were distributed into a 96-well plate and selective medium applied (DMEN, 10% foetal calf serum, 0,8 μg/ml mycophenolic acid, 250 μg/ml xanthine). Transfected clones were visible with the naked eyes 10 days later.

The presence of the human antibody in the medium of wells containing transfected clones was measured by ELISA. Microtiter plate wells were coated with goat anti-human (gamma chain specific, After washing with PBST (phosphate buffered saline containing 0.02% Tween 20, pH 7.5), 100 μl of culture medium from the wells containing transfectants was added to each microtitter well for 1 hour at 370 C. The wells were washed with PBST and the conjugated goat anti-human Kappa, light chain specific were added and incubated at room temperature for one hour. The wells were then washed with PBST and substrate buffer containing dietanolamine added. After 30 minutes the absorbency at 405 nm was measured.

Construction of Humanised IOR C5H by T Epitopes Humanisation.

Prediction of T Epitopes.

The variable region sequences of IOR C5 were analysed using AMPHI program, which predicts segments of the sequences 7 or 11 amino acids in length with an amphipatic helix, which are related with T immunogenicity. Also it was used SOHHA program which predicts hydrophobic helix (Elliot et al. J. Immunol. 138: 2949–2952, (1987). These algorithms predict fragments related with T epitopes presentation in the light and heavy variable regions of the IOR C5.

Analysis of Homology of Variable Regions.

The variable domains of IOR C5 are compared with those corresponding human variable domains, to identify the most homological human sequence with murine molecule. The human sequence databases used were reported in Gene Bank and EMBL, both of them available in Internet. The comparison was made by an automated-computerised method, PC-DOS HIBIO PROSIS 06-00, Hitachi.

Analysis for Immunogenicity Reduction.

The essence of this method lies in reducing the immunogenicity by humanisation of the possible T cell epitopes, with only few mutations in the FRs, specifically in the amphipatic helix, excluded the positions involved with the tridimentional structure of the binding site.

In this method it is compared VH and VK regions of the murine immunoglobuline, with the most homological human immunoglobuline sequence and it could be possible to identify the different residues between murine and human sequences, only inside the amphipatic regions, within the FRs zone (Kabat E.(1991) Sequences of proteins of immunological interest, Fifth Edition, National Institute of Health), only these murine residues will be mutated by those of the human sequence at the same position.

Those residues in the mouse framework responsible for the canonical structures or those involved in the Vernier zone can not be mutate, because they could have a significant effect on the tertiary structure and to affect the binding site. Additional information about the substitutions in the tertiary structure, could be obtain, doing a tridimensional molecular model of the variable regions.

Cloning and Expression of Humanised IOR C5 Antibody into NSO Cells.

After doing PCR overlapping to get mutations and humanised VH and VK, the obtained genetic construction corresponding to IOR C5 by humanisation of T cell epitopes, were cloned into expression vectors in a similar way as used for the expression of the chimeric antibody, yielding the following plasmids: C5Vkhu-PAG4622 and C5Vhhu-PAH4604. The transfection of these genes into NSO cells was done in exactly the same conditions that we previously described for the chimeric antibody.

Obtainment of Single Chain Fv Fragment. Construction and Expression of the scFv.

The strategy includes a first amplification using PCR, which modify VH and VL sequences, including the endonucleases restriction sites to clone in the expression vectors. The amplification used designed oligonucleotides on the exact sequence.

After amplifying, the variable regions are purified and digested with the corresponding restriction enzymes. The DNA fragments are purified and ligated to the expression vectors. Later, these genetic constructions are expressed in *E. coli*, following conventional methods.

In the extraction process of the protein from the producer cells, a rupture process by ultrasound is doing, and it is possible to separate the soluble and insoluble fractions combining SDS polyacrylamide electrophoresis gels, nitrocellulose transfer and western blot.

Partial purification of the protein is carried out by a process which includes: (1) separation of the soluble and insoluble material by ultrasound and centrifugation, (2) Wash in low molarities of urea and solubilization in high concentrations of urea. From solubilized material, to purify the protein by affinity chromatography to metals ions. Later, the protein is renaturalised against buffer.

EXAMPLES

Example 1

Obtainment of the Chimeric Monoclonal Antibody

The VH and VK cDNAs were obtained from RNA extracted from the hybridoma producing the monoclonal antibody IOR C5 using reverse transcriptase enzyme. The specific primers used were:

For VH:

5'-aggtctagaa ctctccacac acaggagagc cagtggatag $\alpha$-3' [SEQ. ID. NO.15]

For VK:

5'-gcgtctagaa ctggatggtg ggaagatgg-3' [SEQ. ID. NO.16].

The ADNc of the chains VH and VK were amplified using polymerase chain reaction (PCR) with Taq polymerase enzyme, and using specific primers ECORV/NHEI restriction site for VH and ECORV/SALI for VK. The specific primers used were:

For VH:

Oligonucleotide 1:

5'-ggggatatcc accatggctg tcttggggct gctcttct-3' [SEQ. ID. NO.17]

Oligonucleotide 2:

5'-tgggtcgaca tgatgggggc tgttgtgcta gctgaggaga c-3' [SEQ. ID. NO.18]

For VK:

Oligonucleotide 1:

5'-ggggatatcc accatgaggg tccccatgac tcagcttct-3' [SEQ. ID. NO.19]

Oligonucleotide 2:

5'-agcgtcgact tacgttttga tttccagact tgtgtccc-3' [SEQ. ID. NO. 20].

The PCR products were cloned in TA vector (TA cloning kit, Invitrogen). Twelve independent clones were sequenced by dideoxy method using T7 DNA Pol (Pharmacia). The VH and VK sequences have high relation with the sub-group 2 of Kabat.

Then, VH chain was digested ECORV/NHEI and VK, ECORWSALI, and cloned in PAH4604 and PAG4622 for VH and VK respectively. These vectors were donated by Sherie Morrison (UCLA, California, USA), and they are used for the immunoglobulines expression in mammalian cells. The PAH 4604 vector has included human constant region IgG1 and the PAG 4622 has human Ck (Novel vectors for the expression of antibody molecules using variable regions generated by polymerase chain reaction., M. Josefina Coloma et al, Journal of Immunological Methods, 152 (1992), 89–104) The resultant constructions after clonig IOR C5 regions were VHC5—PAH4604 and VKC5-PAG4622.

NSO cells were electroporated with 10 ug of the chimeric vector C5VH-PAH4604 and 10 ug of C5VK-PAG4622 and linearized by digestion with Pvul. The DNAs were mixed together, ethanol precipitated and dissolved in 25 ul water. Approximately 107 NSO cells were grown to semi-confluence, harvested by centrifugation and resuspended in 0.5 ml DMEN together with the digested DNA in an electroporation cuvette. After 5 minutes on ice, the cells were given a pulse of 170 volts and 960 uF and left in ice for a further 30 minutes. The cells were then put into 20 ml DMEN plus 10% foetal calf serum and allowed to recover for 48 hours. At this time the cells were distributed into a 96-well plates and selective medium applied (DMEN, 10% foetal calf serum, 10 mM histidinol). Transfected clones were visible with the naked eyes 10 days later.

The presence of chimeric antibody in the medium of wells containing transfected clones was measured by ELISA. Microtiter plate wells were coated with goat anti-human (gamma chain specific, Sara lab). After washing with PBST (phosphate buffered saline containing 0.02% Tween 20, pH 7.5), 20 ul of culture medium from the wells containing transfectants were added to each microtitter well for 1 hour at 370 C. The wells were washed with PBST and alkaline phosphatase conjugated goat anti-human Kappa, light chain specific were added and Incubated at room temperature for one hour. The wells were then washed with PBST and substrate buffer containing dietanolamine added. After 30 minutes the absorbance at 405 nm was measured.

Example 2

Obtainment of Different Versions of Humanised Antibody

The VH and VK IOR C5 sequences were compared with a human sequences database, obtaining the most human homological sequence with the IOR C5.

Then the amphipatic regions or possible T cell epitopes, were determined in VH and VK regions.

For VH, mutations were introduced in positions 10 and 17, and the amino acids ASP and SER by GLY and THR respectively, were substituted. These mutations were done by PCR overlapping, using primers 1 and 2, 3 and 4 in a first PCR and the results of these PCR were overlapped in a second PCR, using 2 and 4 primers, whose sequences are the following: (Kamman, M., Laufs, J., Schell, J., Gronemborg, B. Rapid insertional mutagenesis of DNA by polymerase chain reaction (PCR). Nucleic Acids Research 17:5404, 1989).

Primers for the mutations 10 and 17 of the heavy chain.
Primer 1:
5'-gagtcaggac ctggcctggt gaaaccttct cagacacttt cactcacc-3' [SEQ. ID. NO. 21]
Primer 2:
5'-tgggtcgaca tgatgggggc tgttgtgcta gctgaagaga c-3' [SEQ. ID. NO. 22]
Primer 3:
5'-ggtgagtgaa agtgtctgag aaggtttcac caggccaggt cctgactc-3' [SEQ. ID. NO. 23]
Primer 4:
5'-ggggatatcc accatggctg tcttggggct gctcttct-3' [SEQ. ID. NO. 24].

After the former mutations were verified by sequencing, new mutations were introduced to this mutated DNA, the new mutations introduced in positions 43 and 44 were LYS and GLY, substituting ASN and LYS respectively. The overlapping procedure was done as the previous overlapping. The mutations were verified by sequencing, this new construction was called C5VHhu.

The primers described for these mutations were:
Primers for the mutations 43 and 44 in the heavy chain.
Primer 1:
5'-cagtttccag gaaaaggact ggaatggatg-3' [SEQ. ID. NO. 25]
Primer 2:
5'-tgggtcgaca tgatgggggc tgttgtgcta gctgaagaga c-3' [SEQ. ID. NO. 26]
Primer 3:
5'-catccattcc agtccttttc ctggaaactg-3' [SEQ. ID. NO. 27]
Primer 4:
5'-ggggatatcc accatggctg tcttggggct gctcttct-3' [SEQ. ID. NO. 28].

For VK the mutations were done in positions 15, 45 y 63 substituting ILE, LYS and THR, by LEU, ARG y SER, respectively.

The mutations were introduced by overlapping PCR as describe previously. The sequences of the used primers are shown. The new genetic construction was named C5Vkhu.

Primers for the mutation 15 of the light chain.
Primer 1:
5'-ttgtcggtta cccttggaca accagcc-3' [SEQ. ID. NO. 29]
Primer 2:
5'-agcgtcgact tacgttttga tttccagact tgtgtccc-3' [SEQ. ID. NO. 30]
Primer 3:
5'-ggctggttgt ccaagggtaa ccgacaa-3' [SEQ. ID. NO. 31]
Primer 4:
5'-ggggatatcc accatgaggg tccccatgac tcagcttctc ttggt-3' [SEQ. ID. NO. 32]

Primers for the mutation 45 of the light chain.
Primer 1:
5'-ggccagtctc caaggcgcct aatctat-3' [SEQ. ID. NO. 33]
Primer 2:
5'-agcgtcgact tacgttttga tttccagact tgtgtccc-3' [SEQ. ID. NO. 34]
Primer 3:
5'-atagattagg cgccttggag actggcc-3' [SEQ. ID. NO. 35]
Primer 4:
5'-ggggatatcc accatgaggg tccccatgac tcagcttctc ttggt-3' [SEQ. ID. NO. 36]

Primers for the mutation 63 of the light chain.
Primer 1:
5'-cctgacagat tcagtggcag tggatca-3' [SEQ. ID. NO. 37]
Primer 2:
5'-agcgtcgact tacgttttga tttccagact tgtgtccc-3' [SEQ. ID. NO. 38]
Primer 3:
5'-tgatccactg ccactgaatc tgtcagg-3' [SEQ. ID. NO. 39]
Primer 4:
5'-ggggatatcc accatgaggg tccccatgac tcagcttctc ttggt-3' [SEQ. ID. NO. 40]

All the mutations were verified by sequence.

The humanised VK and VH were cloned into the vectors PAG4622 and PAH4604, the followings constructions were obtained, C5Vkhu-PAG4622 and C5VHhu-PAH4604.

The NSO cells were electroporated with 10 μg of the humanised C5VHhu-PAH4604 and 10 μg of the C5VKhu-PAG4622. These vectors were linearized with PVUI digestion.

The electroporation and detection of the clones expressing humanised antibody IOR C5h were identical to the previous described for the chimeric antibody.

Example 3

Construction of the Single Chain Fv Fragment

Construction of the scFv fragment (VH-linker-VL), from variable domains (VH y VL) of IORC5 mAb. Cloning into expression vector to express in E. Coli.
Procedure (a). Construction of the scFv.

The strategy has a first round of amplification by PCR, modifying sequenced VH and VL regions, including restriction endonucleases sites to cloning into the expression vectors pPACIB.7plus and pPACIB.9plus. In the amplification, the oligonucleotides designed under the exact sequence are used.
Heavy Chain:
4066: EcoRV-FR1-VH
5'-gggatatctg aggtgcagct tcaggagtca gga-3' [SEQ. ID. NO. 41]
4255: EcoRV-FR4-VH
5-caggatatcg cagagacagt gaccagagtc α-3' [SEQ. ID. NO. 42]
Light Chain:
2938: Sal I-FR1-VL
5'-cgtcgacgat atccagatga caccagaact acc-3' [SEQ. ID. NO. 43]
2935: Apa I-FR4-VL
5'-atgggcccctt ttcatgtctc cagcttggt-3' [SEQ. ID. NO. 44].

After amplifying the regions, were purified and digested VH (EcoRV) and VL (SalI-ApaI). The DNA fragments were purified and ligated with pPACIB.9plus and pPACIB.7plus, vectors, previously digested with restriction enzymes.

The plasmid pPACIB.7plus is modified to export to periplasm heterologous proteins whose genes are expressed in *E. coli*. This plasmid contains regulatory sequences to get the following functions: Promoter sequence (tryptophan), sequence for signal peptide (OMPA), sequence for linker peptide (Chaudhary et al., 1990) and a domain composed by 6 hystidines codified in matures protein's C-terminal to help in the purification of this protein (Gavilondo, J. V. et al. Proceedings of the IV Annual Conference on Antibody Engineering. IBC Conferences Inc. Coronado, Calif. Dec. 8–10, 1993).

Figure 1:
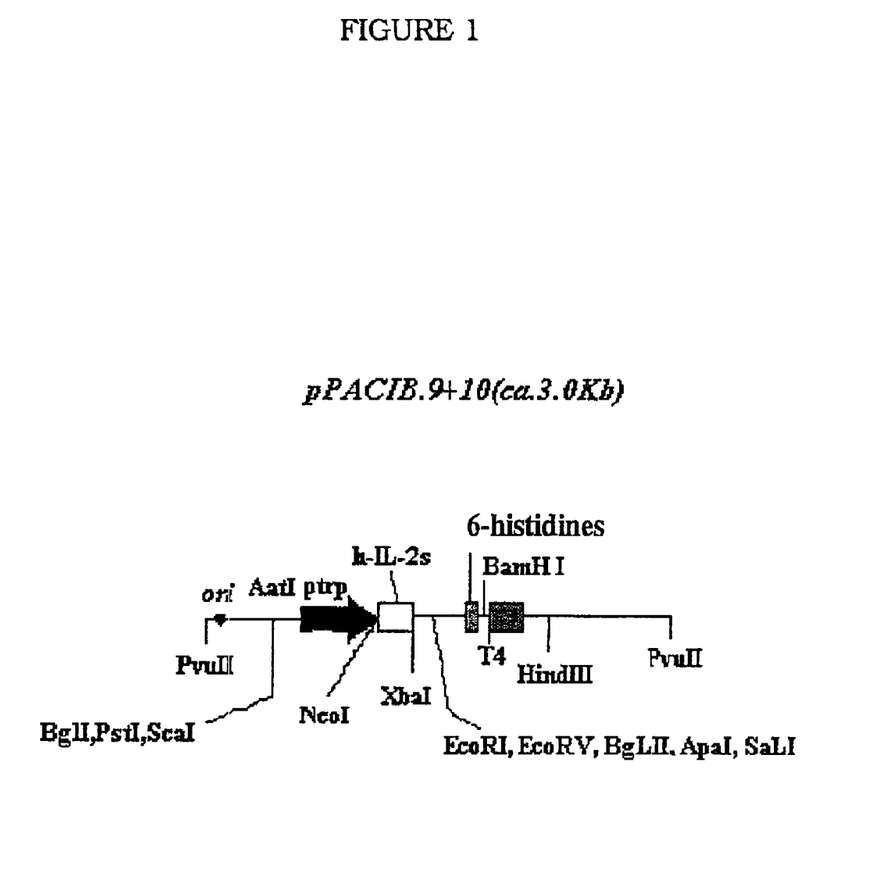
FIG. 1: Shows the genetic construction of the plasmid pPACIB.9plus, which is a modified plasmid to express fusion proteins in the cytoplasm of E. coli. This plasmid contains regulatory sequences to get the following functions: Promoter sequence (tryptophan), 27aa fragment derived from IL-2h for getting efficient expression of the protein and, a domain of 6 histidines codified in mature protein's C-terminal to be used during the purification of this protein.

The plasmid pPACIB.9plus (FIG. 1) is modified to express in the cytoplasm heterologous proteins whose genes are expressed in *E. coli*. This plasmid contains regulatory sequences to get the following functions: Promoter sequence (tryptophan), 27aa fragment derived from IL-2h for getting efficient expression of the protein, and a domain of 6 hystidines codified in matures protein's C-terminal to help in the posterior purification of this protein (Gavilondo, J. V. et al. Proceedings of the IV Annual Conference on Antibody Engineering. IBC Conferences Inc. Coronado, Calif. Dec. 8–10, 1993).

The PCR reaction's product was used to transform the competent *E. coli* cells (strain MC1061), which were plated under solid selective medium and grown at 37° C. To select recombinant vectors, a bacterial colonies were inoculated in liquid medium and extracted plasmid DNA from this culture (Molecular Cloning, A Laboratory Manual, second edition, 1989, Sambrook, Fritsch and Maniatis). The plasmid DNA was digested by EcoRV, SalI/ApaI, XhoI/ApaI according cloning step, after applying under agarose gel and visualised with UV light, the recombinant clones were select between the clones with digestion pattern of two bands, one of them corresponding to pPACIB.7 and 9plus (approx. 2.9 kb), and the second to the expected domain (approx. 320 pb VH or VL y 720 pb for the scFv). For VH domain the insertion orientation was checked by DNA sequencing.

Procedure (b). Expression of scFv in *E. Coli*, Obtained from Variable Domain Genes of IOR C5 Mab.

Four strains of *E. coli* were transformed (TG1, coliB, W3110 y MM294), to study the cloned gene expression, using two recombinant plasmids selected in (a). Basically the recombinant bacteria were grown in liquid medium (LB) with ampicillin, overnight at 37° C. From these cultures, were inoculated fresh cultures containing ampicillin, and incubated by 3 hrs at 37° C. Then, the expression of the protein was induced, adding to the culture beta-indolacrylic acid (inductor of the tryptophan promoter). The analysis of the samples in SDS poliacryilamide gels at 12%, indicated that a protein of approximately of 28 kDa is expressed under these conditions, in the periplasmatic fraction for the construction of pPACIB.7plus and a 30 kDa band for the recombinant clone in pPACIB.9plus, which is expressed in TG1 in between 6–11% of the total bacterial protein. It demonstrated through a Western blot (Molecular Cloning, A Laboratory Manual, second edition de 1989, by Sambrook, Fritsch and Maniatis) with an antisera obtained in rabbit against Fab fragment of IOR C5 Mab, and immunopurified, that this protein corresponds to scFv of IOR C5.

Example 4

Obtention of the scFv from Bacterial Cultures, Renaturalisation and Recognition Assays to Antigen Procedure (a). Extraction and Renaturalisation of the scFv of IOR C5 from Recombinant Clone in pPACIB.9plus.

In the extraction process of the protein from the producer cells using rupture ultrasound process, that allowed to separate soluble and insoluble fractions, combining with SDS-polyacrilamide electrophoresis gels, transferred to nitrocellulose and Western blot, evidenced that the protein remains in the insoluble bacterial fraction.

Under these circumstances the protein was partially purified in a process including the followings steps:

(1) separation of the soluble and insoluble material by ultrasound and centrifugation,
(2) wash in low molarities of urea (2 M) and
(3) solubilization to high molarities of Urea (6 M).

From the solubilized material, the protein is purified in affinity chromatography to metallic ions and renaturalised against buffer solution.

Procedure (b). Binding Assay to Tumour Cells of the scFv-IORC5 Fragment.

Cell Lines:

The cells were obtained from Centro de Immunologla Molecular. SW948 adenocarcinome cell line was grown in L-15 medium supplemented with 10% bovine foetal serum at 37° C. in 6% $CO_2$. Rai cell line (Burkift human limphome) and Hut 78 (T human cell line) were used as negative controls.

These cell lines were grown in RPMI 1629 supplemented with 10% bovine foetal serum at 37° C.

The cell suspensions were fixed to 106 cell/ml in PBS containing 1% albumin of bovine serum. 10 ul of cell suspension was added to each well. The slides were dried in the dusty free air during 3 hours and fixed in acetone-methanol (1:1) solution, 5 minutes, and hydrated in TBS by 10 minutes. Finally, the cells were processed, using immunocytochemistry assay.

The activity of scFv IORC5 fragment was determined using immunocytochemistry assay, trough immunoperoxidase technique. The cells were incubated during 2 hours at 37° C. with single chain Fv IOR C5, followed by incubation with anti Fab serum and with an anti-mouse peroxidase conjugated (HRP0), each one for 30 minutes at room temperature. The localisation site of the peroxidase were visualised with solution which contains 5 mg of 3-3 diaminobencidine, 5 ml of TBS and 5 $\mu$l of H2O2, 30%. Between incubations, the slides were washed with cold TBS.

After introducing in water, the slides were contrasted with Hematoxilline of Mayer and Canadian Balsam was added. Each experiment included positive and negative controls.

The immunocytochemistry studies revealed that this fragment is only positive to SW948 cell line, that showed a moderate labelled comparing with the complete Mab, demonstrated a specific recognition of the scFv IORc5 to this cell line. The label was associated to the membrane and cytoplasm compartment in the malignant colon cells.

What is claimed is:

1. A recombinant antibody recognizing IOR C2 antigen, the recombinant antibody being produced from murine monoclonal antibody IOR C5 produced by the hybridoma deposited with the European Collection of Cell Cultures under accession number 97061101, wherein said recombinant antibody comprises Complementary Determining Regions (CDRs) and framework regions (FRs) of the murine monoclonal IOR C5 and humanized constant regions in its light and heavy chains, and wherein the heavy and light chains comprise at least one framework region point mutation selected from the group consisting of:

Heavy Chain:
  Position 10 ASP for GLY
  Position 17 SER for THR
  Position 43 ASN for LYS
  Position 44 LYS for GLY
Light Chain:
  Position 15 ILE for LEU
  Position 45 LYS for ARG
  Position 63 THR for SER.

2. Cellular line expressing the recombinant antibody of claim 1.

3. Pharmaceutical composition for treating recto and colon malignant tumors, metastasis thereof and recurrences, comprising the recombinant antibody of claim 1 and a suitable excipient.

4. Pharmaceutical composition for localization and identification "in vivo" of recto and colon malignant tumors, metastasis thereof and recurrences, comprising the recombinant antibody of claim 1.

5. Pharmaceutical composition according to claims 3 or 4 comprising also compounds for radiolabeling the antibodies.

6. Pharmaceutical composition according to claim 5 comprising technetium 99, rhenium 186, rhenium 188 or analogues as radiolabelers.

7. A single chan Fv fragment recognizing IOR C2 antigen, the Fv fragment being produced from murine monoclonal antibody IOR C5 produced by the hybridoma deposited with the European Collection of Cell Cultures under accession number 97061101, said Fv fragment containing the complementary Determining Regions (CDRs) and frameworks regions (FRs) of the murine monoclonal antibody IOR C5 and humanized constant regions (FRs) of the murine monoclonal antibody IOR and light chains comprise at least one framework region point mutation selected from the group consisting of:

Heavy Chain:
  Position 10 ASP by GLY
  Position 17 SER by THR
  Position 43 ASN by LYS
  Position 44 LYS by GLY
Light Chain:
  Position 15 ILE by LEU
  Position 45 LYS by ARG
  Position 63 THR by SER.

8. Host cell which expresses the single chain Fv fragment of claim 7.

9. Pharmaceutical composition for treating recto and colon malignant tumors, metastasis thereof and recurrences, comprising the single chain Fv fragment of claim 7 and a suitable excipient.

10. Pharmaceutical composition for localization and identification "in vivo" of recto and colon malignant tumors, metastasis thereof and recurrences, comprising the single chain Fv fragment of claim 7.

11. Pharmaceutical composition according to claims 9 or 10 further comprising compounds for radiolabeling the Fv fragments.

12. Pharmaceutical composition according to claim 11 comprising technetium 99, rhenium 186, rhenium 188 or analogues as radiolabelers.

* * * * *

SEQUENCE LISTING

<160> NUMBER OF SEQ ID NOS: 44

<210> SEQ ID NO 1
<211> LENGTH: 6
<212> TYPE: PRT
<213> ORGANISM: Mus musculus

<400> SEQUENCE: 1

Ser Ala Tyr Asn Trp His
1               5

<210> SEQ ID NO 2
<211> LENGTH: 16
<212> TYPE: PRT
<213> ORGANISM: Mus musculus

<400> SEQUENCE: 2

Thr Ile Ser Thr Asn Gly Thr Thr Ser Tyr Asn Pro Ser Leu Lys Ser
1               5                   10                  15

<210> SEQ ID NO 3
<211> LENGTH: 9
<212> TYPE: PRT
<213> ORGANISM: Mus musculus

<400> SEQUENCE: 3

Asn Asp Glu Arg Ala Trp Phe Ala Tyr
1               5

<210> SEQ ID NO 4
<211> LENGTH: 16
<212> TYPE: PRT
<213> ORGANISM: Mus musculus

<400> SEQUENCE: 4

Leu Ser Ser Gln Ser Leu Leu Asp Ser Asp Gly Leu Tyr Tyr Leu Asn
1               5                   10                  15

<210> SEQ ID NO 5
<211> LENGTH: 7
<212> TYPE: PRT
<213> ORGANISM: Mus musculus

<400> SEQUENCE: 5

Leu Val Ser Lys Leu Asp Ser
1               5

<210> SEQ ID NO 6
<211> LENGTH: 9
<212> TYPE: PRT
<213> ORGANISM: Mus musculus

<400> SEQUENCE: 6

Trp Gln Gly Thr His Phe Pro His Thr
1               5

<210> SEQ ID NO 7
<211> LENGTH: 30
<212> TYPE: PRT
<213> ORGANISM: Mus musculus

<400> SEQUENCE: 7

Asp Val Gln Leu Gln Glu Ser Gly Pro Gly Leu Val Lys Pro Ser Gln

-continued

```
                1               5                  10                 15
Thr Leu Ser Leu Thr Cys Thr Val Thr Gly Thr Ser Ile Thr
                20                 25                 30

<210> SEQ ID NO 8
<211> LENGTH: 14
<212> TYPE: PRT
<213> ORGANISM: Mus musculus

<400> SEQUENCE: 8

Trp Ile Arg Gln Phe Pro Gly Lys Gly Leu Glu Thr Met Gly
1               5                  10

<210> SEQ ID NO 9
<211> LENGTH: 32
<212> TYPE: PRT
<213> ORGANISM: Mus musculus

<400> SEQUENCE: 9

Arg Ile Ser Ile Thr Arg Asp Thr Ser Lys Asn Gln Phe Phe Leu Gln
1               5                  10                 15

Leu Asn Ser Val Thr Thr Glu Asp Thr Ala Thr Tyr Tyr Cys Ala Arg
                20                 25                 30

<210> SEQ ID NO 10
<211> LENGTH: 11
<212> TYPE: PRT
<213> ORGANISM: Mus musculus

<400> SEQUENCE: 10

Trp Gly Gln Gly Thr Leu Val Thr Val Ser Ala
1               5                  10

<210> SEQ ID NO 11
<211> LENGTH: 23
<212> TYPE: PRT
<213> ORGANISM: Mus musculus

<400> SEQUENCE: 11

Asp Trp Trp Met Thr Gln Thr Pro Leu Thr Leu Ser Val Thr Leu Gly
1               5                  10                 15

Gln Pro Ala Ser Ile Ser Cys
                20

<210> SEQ ID NO 12
<211> LENGTH: 15
<212> TYPE: PRT
<213> ORGANISM: Mus musculus

<400> SEQUENCE: 12

Trp Leu Leu Gln Arg Pro Gly Gln Ser Pro Arg Arg Leu Ile Tyr
1               5                  10                 15

<210> SEQ ID NO 13
<211> LENGTH: 32
<212> TYPE: PRT
<213> ORGANISM: Mus musculus

<400> SEQUENCE: 13

Gly Val Pro Asp Arg Phe Ser Gly Ser Gly Ser Gly Thr Asp Phe Ala
1               5                  10                 15

Leu Lys Ile Arg Arg Val Glu Ala Glu Asp Leu Gly Val Tyr Tyr Cys
                20                 25                 30
```

<210> SEQ ID NO 14
<211> LENGTH: 17
<212> TYPE: PRT
<213> ORGANISM: Mus musculus

<400> SEQUENCE: 14

Phe Gly Gly Gly Thr Lys Leu Glu Ile Lys Arg Lys Ser Thr Leu Thr
1               5                   10                  15

Gly

<210> SEQ ID NO 15
<211> LENGTH: 42
<212> TYPE: DNA
<213> ORGANISM: Mus musculus

<400> SEQUENCE: 15
aggtctagaa ctctccacac acaggagagc cagtggatag ac                          42

<210> SEQ ID NO 16
<211> LENGTH: 29
<212> TYPE: DNA
<213> ORGANISM: Mus musculus

<400> SEQUENCE: 16
gcgtctagaa ctggatggtg ggaagatgg                                         29

<210> SEQ ID NO 17
<211> LENGTH: 38
<212> TYPE: DNA
<213> ORGANISM: Mus musculus

<400> SEQUENCE: 17
ggggatatcc accatggctg tcttggggct gctcttct                               38

<210> SEQ ID NO 18
<211> LENGTH: 41
<212> TYPE: DNA
<213> ORGANISM: Mus musculus

<400> SEQUENCE: 18
tgggtcgaca tgatgggggc tgttgtgcta gctgaggaga c                           41

<210> SEQ ID NO 19
<211> LENGTH: 39
<212> TYPE: DNA
<213> ORGANISM: Mus musculus

<400> SEQUENCE: 19
ggggatatcc accatgaggg tccccatgac tcagcttct                              39

<210> SEQ ID NO 20
<211> LENGTH: 38
<212> TYPE: DNA
<213> ORGANISM: Mus musculus

<400> SEQUENCE: 20
agcgtcgact tacgttttga tttccagact tgtgtccc                               38

<210> SEQ ID NO 21
<211> LENGTH: 48
<212> TYPE: DNA
<213> ORGANISM: Mus musculus

```
<400> SEQUENCE: 21
gagtcaggac ctggcctggt gaaaccttct cagacacttt cactcacc          48

<210> SEQ ID NO 22
<211> LENGTH: 41
<212> TYPE: DNA
<213> ORGANISM: Mus musculus

<400> SEQUENCE: 22
tgggtcgaca tgatggggc tgttgtgcta gctgaagaga c                  41

<210> SEQ ID NO 23
<211> LENGTH: 48
<212> TYPE: DNA
<213> ORGANISM: Mus musculus

<400> SEQUENCE: 23
ggtgagtgaa agtgtctgag aaggtttcac caggccaggt cctgactc          48

<210> SEQ ID NO 24
<211> LENGTH: 38
<212> TYPE: DNA
<213> ORGANISM: Mus musculus

<400> SEQUENCE: 24
ggggatatcc accatggctg tcttggggct gctcttct                     38

<210> SEQ ID NO 25
<211> LENGTH: 30
<212> TYPE: DNA
<213> ORGANISM: Mus musculus

<400> SEQUENCE: 25
cagtttccag gaaaaggact ggaatggatg                              30

<210> SEQ ID NO 26
<211> LENGTH: 41
<212> TYPE: DNA
<213> ORGANISM: Mus musculus

<400> SEQUENCE: 26
tgggtcgaca tgatggggc tgttgtgcta gctgaagaga c                  41

<210> SEQ ID NO 27
<211> LENGTH: 30
<212> TYPE: DNA
<213> ORGANISM: Mus musculus

<400> SEQUENCE: 27
catccattcc agtccttttc ctggaaactg                              30

<210> SEQ ID NO 28
<211> LENGTH: 38
<212> TYPE: DNA
<213> ORGANISM: Mus musculus

<400> SEQUENCE: 28
ggggatatcc accatggctg tcttggggct gctcttct                     38

<210> SEQ ID NO 29
<211> LENGTH: 27
<212> TYPE: DNA
```

<213> ORGANISM: Mus musculus

<400> SEQUENCE: 29
ttgtcggtta cccttggaca accagcc                                   27

<210> SEQ ID NO 30
<211> LENGTH: 38
<212> TYPE: DNA
<213> ORGANISM: Mus musculus

<400> SEQUENCE: 30
agcgtcgact tacgttttga tttccagact tgtgtccc                        38

<210> SEQ ID NO 31
<211> LENGTH: 27
<212> TYPE: DNA
<213> ORGANISM: Mus musculus

<400> SEQUENCE: 31
ggctggttgt ccaagggtaa ccgacaa                                   27

<210> SEQ ID NO 32
<211> LENGTH: 45
<212> TYPE: DNA
<213> ORGANISM: Mus musculus

<400> SEQUENCE: 32
ggggatatcc accatgaggg tccccatgac tcagcttctc ttggt               45

<210> SEQ ID NO 33
<211> LENGTH: 27
<212> TYPE: DNA
<213> ORGANISM: Mus musculus

<400> SEQUENCE: 33
ggccagtctc caaggcgcct aatctat                                   27

<210> SEQ ID NO 34
<211> LENGTH: 38
<212> TYPE: DNA
<213> ORGANISM: Mus musculus

<400> SEQUENCE: 34
agcgtcgact tacgttttga tttccagact tgtgtccc                        38

<210> SEQ ID NO 35
<211> LENGTH: 27
<212> TYPE: DNA
<213> ORGANISM: Mus musculus

<400> SEQUENCE: 35
atagattagg cgccttggag actggcc                                   27

<210> SEQ ID NO 36
<211> LENGTH: 45
<212> TYPE: DNA
<213> ORGANISM: Mus musculus

<400> SEQUENCE: 36
ggggatatcc accatgaggg tccccatgac tcagcttctc ttggt               45

<210> SEQ ID NO 37
<211> LENGTH: 27

```
<212> TYPE: DNA
<213> ORGANISM: Mus musculus

<400> SEQUENCE: 37
cctgacagat tcagtggcag tggatca                                27

<210> SEQ ID NO 38
<211> LENGTH: 38
<212> TYPE: DNA
<213> ORGANISM: Mus musculus

<400> SEQUENCE: 38
agcgtcgact tacgttttga tttccagact tgtgtccc                    38

<210> SEQ ID NO 39
<211> LENGTH: 27
<212> TYPE: DNA
<213> ORGANISM: Mus musculus

<400> SEQUENCE: 39
tgatccactg ccactgaatc tgtcagg                                27

<210> SEQ ID NO 40
<211> LENGTH: 45
<212> TYPE: DNA
<213> ORGANISM: Mus musculus

<400> SEQUENCE: 40
ggggatatcc accatgaggg tccccatgac tcagcttctc ttggt            45

<210> SEQ ID NO 41
<211> LENGTH: 33
<212> TYPE: DNA
<213> ORGANISM: Mus musculus

<400> SEQUENCE: 41
gggatatctg aggtgcagct tcaggagtca gga                         33

<210> SEQ ID NO 42
<211> LENGTH: 32
<212> TYPE: DNA
<213> ORGANISM: Mus musculus

<400> SEQUENCE: 42
caggatatcg cagagacagt gaccagagtc cc                          32

<210> SEQ ID NO 43
<211> LENGTH: 33
<212> TYPE: DNA
<213> ORGANISM: Mus musculus

<400> SEQUENCE: 43
cgtcgacgat atccagatga caccagaact acc                         33

<210> SEQ ID NO 44
<211> LENGTH: 29
<212> TYPE: DNA
<213> ORGANISM: Mus musculus

<400> SEQUENCE: 44
atgggccctt ttcatgtctc cagcttggt                              29
```